United States Patent [19]

Nakajima et al.

[11] Patent Number: 5,026,395
[45] Date of Patent: Jun. 25, 1991

[54] INTRAOCULAR LENS HAVING A COATING LAYER AND A METHOD FOR MANUFACTURING THE SAME

[75] Inventors: Ikuo Nakajima, Tokyo; Moriyuki Okamura, Sagamihara; Toshiji Nishiguchi, Kanagawa, all of Japan

[73] Assignee: Canon Kabushiki Kaisha, Tokyo, Japan

[21] Appl. No.: 356,560

[22] Filed: May 25, 1989

[30] Foreign Application Priority Data

May 31, 1988 [JP] Japan .................. 63-133154

[51] Int. Cl.$^5$ .............................................. A61F 2/16
[52] U.S. Cl. .......................................................... 623/6
[58] Field of Search .................................. 623/6–66; 351/163–167

[56] References Cited

U.S. PATENT DOCUMENTS

| 4,312,575 | 1/1982 | Penman et al. | 351/160 |
| 4,822,359 | 4/1989 | Tano et al. | 623/6 |
| 4,872,877 | 10/1989 | Tiffony | 623/6 |
| 4,919,659 | 4/1990 | Horbett et al. | 623/66 |

Primary Examiner—D. Isabella
Attorney, Agent, or Firm—Fitzpatrick, Cella, Harper & Scinto

[57] ABSTRACT

An intraocular lens having a lens base and a coating layer disposed on or otherwise operably associated with a first surface of the lens base. The coating layer is formed by, for example, plasma polymerization of a monomer gas while simultaneously sublimating or evaporating an ultraviolet absorber, thereby forming an intraocular lens which absorbs ultraviolet rays and prevents any free monomer or other substance from oozing out of the lens base and permeating the eye. The properties of the intraocular lens can be readily varied by selecting different monomer gases.

6 Claims, 1 Drawing Sheet

# INTRAOCULAR LENS HAVING A COATING LAYER AND A METHOD FOR MANUFACTURING THE SAME

BACKGROUND OF THE INVENTION

1. Field of the Invention

This invention relates to an intraocular lens (substitute for human lens) having a coating layer formed on its surface and to a method of manufacturing this type of lens.

2. Description of the Prior Art

Conventionally, in the treatment of cataracts, the clouded lens is enucleated by surgery, and an artificial lens is implanted in the capsula lentis, thereby enabling recovery of vision after the operation. Use of the in-the-bag method which is considered to enable implantation of such an intraocular lens with fewer complications, namely, the method of inserting the intraocular lens in the capsula lentis, is now becoming a mainstream practice.

Ordinarily, this type of intraocular lens is formed of a material constituted mainly by polymethyl methacrylate, while a lens support called harptic is formed of a material such as polymethyl methacrylate, polyvinylidene fluoride or the like.

With respect to this conventional intraocular lens, problems are encountered due to a free monomer of polymethyl methacrylate which oozes out and permeates the eye.

U.S. Pat. No. 4,312,575 is directed to an intraocular lens designed to form a coating on its surface by plasma polymerization in order to prevent the flow of a free monomer into the eye.

U.S. Pat. No. 4,312,575 also states that a coloring material may be mixed in the base material of an intraocular lens before application of the coating layer in order to adapt the lens to absorb ultraviolet rays harmful to the retina.

However, mixing an ultraviolet ray absorbing substance in the base material of the intraocular lens reduces the mechanical strength of the lens.

SUMMARY OF THE INVENTION

It is an object of the present invention to provide an intraocular lens having various properties including that of absorbing ultraviolet rays and of preventing any free monomer from oozing out and permeating the eye, while maintaining its desired mechanical strength, and also to provide a method of manufacturing this lens.

To this end, the present invention provides an intraocular lens having a coating layer which is formed on or otherwise operably associated with a surface of the lens base and in which an ultraviolet absorber is mixed.

The present invention also provides a method of manufacturing an intraocular lens by forming a coating layer on or otherwise operably associated with a surface of the lens base by plasma polymerization while sublimating or evaporating an ultraviolet absorber to mix the same in the coating layer.

DESCRIPTION OF THE PREFERRED EMBODIMENTS

Figure 1:
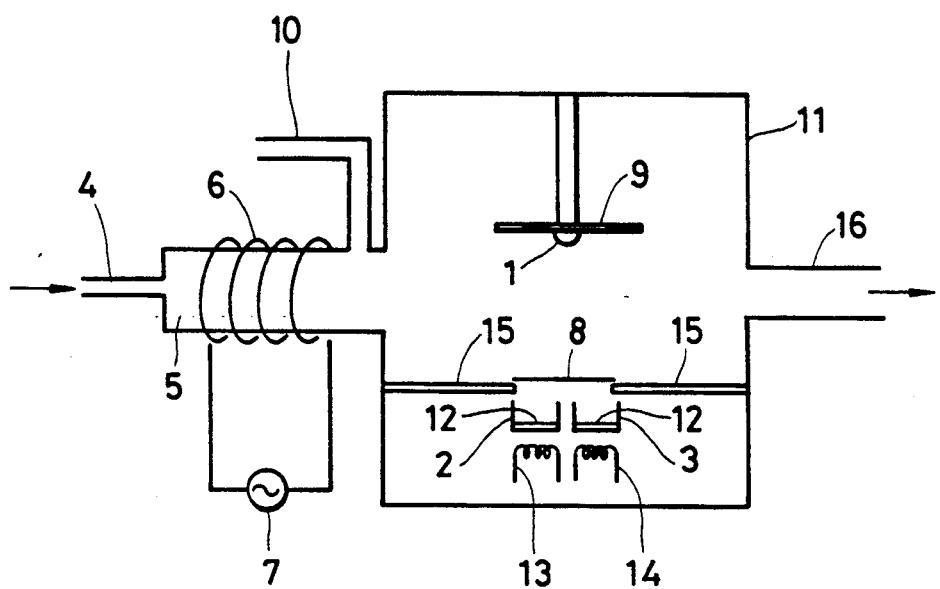
FIG. 1 is a schematic side view of a plasma polymerization apparatus used in accordance with the present invention.

An intraocular lens in accordance with the present invention has a coating layer which is formed on or otherwise operably associated with a surface of the lens base and in which an ultraviolet absorber is mixed. A well-known conventional intraocular lens may be directly utilized as the lens base in accordance with the present invention. Preferably, the lens base is formed of a material such as polymethyl methacrylate, hydroxyethyl methacrylate, silicone resin or polyurethane resin.

As will be explained later, the coating layer is, preferably, a film plasma-polymerized from a monomer gas. The coating layer can be provided with various properties depending upon the kind or composition of the monomer gas.

To enable the coating layer to have hydrophilic properties, the monomer gas may be formed from a hydrocarbon, a nitro-compound, an amino-compound, a cyan compound, a silicone compound or the like. More preferably, the monomer gas may be formed from a material selected from saturated or unsaturated hydrocarbons such as methane, ethane, propane, butane, pentane, hexane, cyclohexane, ethylene, propylene, butylene, pentene, acetylene and cyclohexene, saturated or unsaturated fatty nitro-compounds such as nitromethane, nitroethane, 1-nitropropane, 2-nitropropane, 1-nitrobutane, 2-nitrobutane, 2-methyl-1-nitropropane, 1-nitropentane, 1-nitrohexane, 2-nitrohexane, 1-nitropropane, 2-methyl-1-nitropropane and 1-nitrodecane, saturated or unsaturated fatty amino-compounds such as aminoethane, 1-aminopropane, 2-aminopropane, 1-aminobutane, 2-aminobutane, 1-amino-2-methylpropane, 1-aminopentane, 1-aminohexane, 1-aminoheptane, 1-amino-octane, 1-aminononane, 1-aminodecane, aminoethylene, 1-aminopropene and 1-aminobutene, saturated or unsaturated fatty cyano-compounds such as cyanomethane, cyanoethane, cyanopropane, cyanobutane, 1-cyanopropane, 2-cyanopropane, 1-cyanobutane, 2-cyanobutane, 1-cyano-2-methylpropane, 1-cyanopentane, 1-cyanohexane, 1-cyanoheptane, 1-cyano-octane, 1-cyanononane, 1-cyanodecane, cyanoethylene, 1-cyanopropene and 1-cyanobutene; and organosilane compounds such as tetraethoxysilane, vinyltriethylsilane, tetravinylsilane, hexamethyldisilane, tetramethylsilane, tetraethylsilane, tetramethoxysilane, vinyltriacetoxysilane, vinyltriethoxysilane and vinyltrimethoxysilane.

A monomer for enabling the coating layer to prevent any free monomer or other chemical compounds from being eluted from the lens base may be selected from hydrocarbons, nitro-compounds, silicone compounds, fluorine compounds and the like. The above examples of hydrocarbons and nitro-compounds can also be used as such a monomer, and examples of fluorine compounds are tetrafluoromethane, hexafluoroethane, tetrafluoroethylene and octafluoropropane.

To enable the coating layer to possess wear-resistant properties, the monomer gas may be formed from a material selected from the above hydrocarbons and fluorine compounds or from heterocyclic compounds such as 2-pyrrolidone and N-pyrrolidone.

The plasma-polymerized coating layer in accordance with the present invention may be formed from one of the above hydrocarbons, nitro-compounds, amino-compounds, cyano-compounds, silicone compounds, fluorine compounds and heterocyclic compounds or a mixture of at least two of these compounds.

An ultraviolet absorber to be mixed in the coating layer may be one of aromatic compounds such as benzotriazole, benzophenone, benzene, naphthalene, phenanthrene, anthracene, naphthacene, o-nitrophenol, m-nitrophenol, p-nitrophenol, o-nitroaniline, m-nitroaniline, p-nitroaniline, quinoline, isoquinoline, pyrimidine and acridine or a mixture of at least two of these compounds. Each of these compounds can be sublimated or evaporated by heating for formation of the layer in a chamber 11 of a vacuum reactor shown in FIG. 1.

The intraocular lens in accordance with the present invention may have an intermediate layer formed between the lens base and the coating layer in which an ultraviolet absorber is mixed, or may have, on the coating layer in which an ultraviolet absorber is mixed, another coating layer having different properties.

The ultraviolet absorber is sublimated or evaporated by heating to be mixed in the coating layer during plasma polymerization of the monomer gas for formation of the coating layer.

Next, formation of the coating layer will be described with reference to FIG. 1.

A lens base 1 is mounted to a support 9 of the chamber 11. An ultraviolet absorber 12 is placed at a position opposite to the lens base 1 with a shutter 8 and a partition wall 15 interposed therebetween. The ultraviolet absorber 12 is contained in receptacles 2 and 3. Heaters 13 and 14 are provided below the receptacles 2 and 3 to heat up the ultraviolet absorber 12.

The chamber 11 is provided with a drawing pipe 5 and a discharge pipe 14. The drawing pipe 5 is connected to gas inlet pipes 4 and 10. Ordinarily, a monomer gas is introduced into the chamber 11 through the inlet pipe 10 while a carrier gas is introduced through the inlet pipe 4. The carrier gas is introduced if it is necessary to limit dissociation of the monomer gas. An inert gas (e.g., argon gas) is used as the carrier gas. However, in the examples of the process of the present invention described later, a carrier gas was not used when introducing a monomer gas into the chamber 11 through the inlet pipe 4. In this instance, the inlet pipe 10 is closed.

A coil 6 is wound around the drawing pipe 5. The coil 6 is supplied with an electric current from a power source 7.

Operation of this apparatus will be described below. The discharge pipe 16 is first evacuated by a vacuum pump (not shown) so that the pressure inside the chamber 11 becomes equal to or lower than a predetermined value, e.g., 1 mm Torr. Thereafter, the ultraviolet absorber 12 is heated to a predetermined temperature, e.g., 50° to 500° C., and a monomer to be plasma-polymerized is introduced through the inlet pipe 4. Then, the coil 6 is supplied with a current from the power source 7, thereby initiating glow discharge. After initiating glow discharge, the shutter 8 is opened to enable volatilized components of the ultraviolet absorber 12 to reach the lens base 1. The ultraviolet absorber 12 is thereby introduced into the plasma-polymerized layer, thus forming on the lens base 1 a coating layer in which the ultraviolet absorber 12 is mixed. It is possible to form the coating layer uniformly by changing the posture or placement of the lens base 1 (e.g., turning the base upside down).

Conditions for plasma polymerization can be determined on the basis of the conditions for an ordinary plasma polymerization reaction. For example, the chamber 11 is evacuated at a pressure of not higher than 1 mm Torr, and the monomer is thereafter introduced into the chamber 11 at a rate of 100 SCMM per minute or less, more preferably, 20 SCCM or less until the pressure inside the chamber 11 is adjusted to a value of about 0.01 to 10 Torr. The discharge output is maintained at 300 W or less, more preferably, 100 W or less.

The period of time to form the layer of the present invention varies depending upon the thickness of the coating layer formed on the lens base 1. The thickness of the coating layer is not specifically limited and it may be ordinarily 50 to 20000 Å or, preferably, 50 to 3000 Å. The required layer formation time is therefore short, e.g., not longer than several dozen minutes.

The present invention will be described below in more detail with respect to specific examples thereof.

EXAMPLE 1

A member formed from a silicone resin, e.g., polydimethylsiloxane and having a thickness of 1 mm at its thickest portion and a diameter of 7 mm was mounted as the lens base 1 to the support 9 of the vacuum reactor shown in FIG. 1. Benzotriazole was used as the ultraviolet absorber 12 and was placed in the ultraviolet absorber receptacles 2 and 3. The pressure inside the chamber 11 was maintained at $1 \times 10^3$ Torr and the receptacles 2 and 3 were constantly heated at 300° C. Methane and tetramethylsilane were used as monomers to be plasma-polymerized. Methane and tetramethylsilane were introduced into the chamber 1 through the inlet pipe 4 at 10 SCCM and at 5 SCCM, respectively, while the pressure inside the chamber 11 was maintained at 10 mm Torr. High-frequency power having a frequency of 13.56 MHz was supplied to the coil 6, and the discharge power was adjusted to 50 W. In this state, the shutter 8 was opened for 90 seconds for layer formation. As a result, an intraocular lens having on its surface a coating layer in which the ultraviolet absorber was mixed was obtained.

The thickness of the coating layer formed on the surface of the intraocular lens was obtained by measuring the thickness of a coating layer which was formed over a surface of a silicone wafer placed by the side of the lens base 1 while the ultraviolet absorber was introduced into the layer. The thickness of the coating layer on the wafer surface was measured by the contact method. The obtained thickness was 1000 Å±100 Å. The results of the measurements of the spectral transmittance of the obtained intraocular lens using a spectrophotometer (U-3400, product of Hitachi, ltd.) are shown in Table 1.

The angle of contact of water with the obtained intraocular lens was measured by the liquid-drop method. The contact angle was measured after a predetermined number of days in order to examine changes in the contact angle over time. These results, shown in Table 2, when considered long with the results in Table 1 demonstrate that the intraocular lens of Example 1 absorbs ultraviolet rays while still maintaining its durability.

EXAMPLE 2

Methane and N-vinylpyrrolidone were used as the monomers to be plasma-polymerized. Methane was introduced into the chamber 11 at 5 SCCM while N-vinylpyrrolidone was introduced at 15 SCCM. The discharge power was adjusted to 30 W. Except for these conditions the process was conducted in the same manner as Example 1 and produced an intraocular lens having a coating layer in which the ultraviolet absorber was mixed.

The spectral transmittance and the contact angle were measured with respect to the obtained intraocular lens in the same manner as Example 1. The results of these measurements are shown in Tables 1 and 2.

EXAMPLE 3

Ethane (supplied at 5 SCCM) and allylamine (supplied at 5 SCCM) were used as the monomers to be plasma-polymerized, benzophenone was used as the ultraviolet absorber, the discharge power was adjusted to 20 W, and the layer formation time was 120 seconds. The intraocular lens of this example was manufactured in the same manner as Example 1 except for these parameters.

The spectral transmittance and the contact angle were measured with respect to the obtained intraocular lens in the same manner as Example 1. The results of these measurements are shown in Tables 1 and 2.

EXAMPLE 4

An intraocular lens was manufactured in the same manner as Example 1 except that anthracene was used as the ultraviolet absorber.

The spectral transmittance and the contact angle were measured with respect to the obtained intraocular lens in the same manner as Example 1 and the results are shown in Tables 1 and 2.

EXAMPLE 5

An intraocular lens was manufactured in the same manner as Example 1 except phenanthrene was used as the ultraviolet absorber.

The spectral transmittance and the contact angle were measured with respect to the obtained intraocular lens in the same manner as Example 1 and the results are shown in Tables 1 and 2.

EXAMPLE 6

An intraocular lens was manufactured in the same manner as Example 1 except that a polymethyl methacrylate member having a thickness of 1 mm at its thickest portion and a diameter of 7 mm was used as the lens base 1.

The spectral transmittance and the contact angle were measured with respect to the obtained intraocular lens in the same manner as Example 1. The results of these measurements are shown in Tables 1 and 2.

REFERENCE EXAMPLE 1

The spectral transmittance and the contact angle were measured in the same manner as Example 1 with respect to an intraocular lens having the same lens base as Examples 1 to 5 without a coating layer formed thereon. The results of these measurements are shown in Tables 1 and 2.

REFERENCE EXAMPLE 2

The spectral transmittance and the contact angle were measured in the same manner as Example 1 with respect to an intraocular lens having the same lens base as Example 6 without a coating layer formed thereon. The results of these measurements are shown in Tables 1 and 2.

REFERENCE EXAMPLE 3

An intraocular lens was manufactured in the same manner as Example 1 except that no ultraviolet absorber was used.

The spectral transmittance and the contact angle were measured with respect to the obtained intraocular lens in the same manner as Example 1 and the results are shown in Tables 1 and 2.

As a result of the measurements with respect to Examples 1 to 6, it is readily apparent that the spectral transmittance of each example was not changed substantially even after 200 days. Also the ultraviolet shielding properties thereof were very stable. The measurements the results of which are shown in Table 1 were conducted prior to the standing for 200 days.

The contact angle was measured with respect to the intraocular lenses of Examples 1 to 6 after each lens had been rubbed by a pair of fingers 2000 times while submerged in water. As shown in Table 3, the results of these measurements were the same as the results of the measurements taken prior to the rubbing operation. It was thereby proved that the intraocular lens in accordance with the present invention possessed the desired wear-resistant properties.

An elution test was performed with respect to the intraocular lens of Examples 1 to 6 on the basis of the Notification from the Director of Pharmaceutical Affairs Bureau (Yakumu-kyoku-cho Tsuchi) No. 489, May 10, 1985 "About Intraocular Lens Authorization Criteria" issued from the Ministry of Health and Welfare (Kosei-sho). As a result, as shown in Table 4, properties of each intraocular lens were satisfactory.

EXAMPLE 7

The intraocular lens of Example 1 was folded double by a pair of fingers and no change was observed in the appearance of the intraocular lens. Moreover, the lens was restored to its original state after being released from the fingers.

The tensile strength of the intraocular lens of Example 1 was measured on the basis of JIS 6301, and determined to be 50 kg/cm$^2$.

REFERENCE EXAMPLE 4

An intraocular lens, without a coating layer, was formed from a silicone resin including benzophenone as an ultraviolet absorber. The shape of this intraocular lens was the same as Example 7.

This intraocular lens was folded double by the fingers resulting in a crack extending to an internal portion of the lens. The lens possessed a tensile strength of 8 kg/m$^2$ which was obtained in the same manner as Example 7.

TABLE 1

| Wavelength (nm) | Transmission (%) | | | | |
|---|---|---|---|---|---|
| | 300 | 350 | 400 | 500 | 600 |
| Ex. 1 | <1.0 | <1.0 | 19 | 94.0 | 94.0 |
| Ex. 2 | <1.0 | <1.0 | 15 | 94.0 | 94.0 |
| Ex. 3 | <1.0 | <1.0 | 14 | 94.0 | 94.0 |
| Ex. 4 | <1.0 | <1.0 | 19 | 94.0 | 94.0 |
| Ex. 5 | <1.0 | <1.0 | 18 | 94.0 | 94.0 |
| Ex. 6 | <1.0 | <1.0 | 10 | 94.0 | 94.0 |
| Ref. Ex. 1 | 85 | 92 | 93 | 94.0 | 94.0 |
| Ref. Ex. 2 | 82 | 92 | 92 | 93.0 | 93.0 |
| Ref. Ex. 3 | 0 | 45 | 94 | 94.0 | 94.0 |

TABLE 2

| Lapse of days | Contact Angel ($\theta°$) | | | | | | | |
|---|---|---|---|---|---|---|---|---|
| | 0 | 10 | 20 | 50 | 80 | 120 | 160 | 200 |
| Ex. 1 | 35 | 35 | 35 | 37 | 37 | 37 | 36 | 36 |
| Ex. 2 | 32 | 33 | 33 | 33 | 33 | 33 | 33 | 34 |
| Ex. 3 | 38 | 38 | 38 | 38 | 39 | 38 | 38 | 39 |
| Ex. 4 | 35 | 35 | 36 | 36 | 36 | 36 | 36 | 36 |
| Ex. 5 | 35 | 35 | 35 | 34 | 35 | 35 | 35 | 35 |
| Ex. 6 | 35 | 35 | 35 | 35 | 35 | 35 | 35 | 35 |
| Ref. Ex. 1 | 120 | 120 | 120 | 120 | 120 | 120 | 120 | 120 |
| Ref. Ex. 1 | 65 | 65 | 65 | 65 | 65 | 65 | 65 | 65 |
| Ref. Ex. 3 | 35 | 35 | 35 | 36 | 36 | 36 | 36 | 36 |

TABLE 3

| | Angle of Contact ($\theta°$) | |
|---|---|---|
| | Before rubbing 2000 times | After rubbing 2000 times |
| Ex. 1 | 36 | 35 |
| Ex. 2 | 34 | 35 |
| Ex. 3 | 39 | 39 |
| Ex. 4 | 36 | 38 |
| Ex. 5 | 35 | 35 |
| Ex. 6 | 35 | 36 |

TABLE 4

| | Ex. 1 | Ex. 2 | Ex. 3 | Ex. 4 | Ex. 5 | Ex. 6 | Reference |
|---|---|---|---|---|---|---|---|
| (1) Elution test using $Na_2CO_3$ | | | | | | | |
| (a) Standing at 37° C. for 24 hours | No extraneous substance, not colored | ← | ← | ← | ← | ← | ← |
| (b) after boling for 10 minutes | same as above | ← | ← | ← | ← | ← | ← |
| (2) Elution test using citric acid | | | | | | | |
| (a) Standing at 37° C. for 24 hours | same as above | ← | ← | ← | ← | ← | ← |
| (b) After boiling for 10 minutes | same as above | ← | ← | ← | ← | ← | ← |
| (3) Elution test using water | | | | | | | |
| (a) Appearance | Color, transparent, no extraneous substance | ← | ← | ← | ← | ← | ← |
| (b) Difference of PH from that of reference solution (7.70) | 0.48 | 0.55 | 0.39 | 0.42 | 0.37 | 0.40 | 0.10> |
| (c) Foaming | Same as water | ← | ← | ← | ← | ← | Not large |
| (d) Heavy metal | Same as coloring of reference solution | ← | ← | ← | ← | ← | Lighter than coloring of reference solution |
| (e) Potassium permanganate reducing substance | Difference of $KMnO_4$ consumption rate: 0.42 ml | 0.39 | 0.72 | 0.46 | 0.45 | 0.55 | 0.10> |
| (f) UV spectrum | | | | | | | |
| Wavelength | 220, 250, 350 | 220, 250, 350 | 220, 250, 350 | 220, 250, 350 | 220, 250, 350 | 220, 250, 350 | 220 to 350 nm |
| Absorption | 0.10, 0.03, 0 | 0.01, 0.04, 0 | 0.01, 0.05, 0 | 0.02, 0.05, 0 | 0.01, 0.05, 0 | 0.01, 0.03, 0 | 0.01, 0.02, 0 | 0.10> |

As described above, the present invention makes it possible to manufacture an intraocular lens capable of absorbing ultraviolet rays without reducing the mechanical strength of the lens, and the invention also enables the intraocular lens to have various properties.

What is claimed is:

1. An intraocular lens comprising a lens base and a coating layer on at least a first surface of said lens base, said coating layer being a plasma-polymerized layer separate from said lens base and including an ultraviolet absorber mixed therein.

2. An intraocular lens according to claim 1, wherein said lens base is formed of a material which includes at least one material selected from the group consisting of polymethyl methacrylate, hydroxyethyl methacrylate, silicone resin and polyurethane resin.

3. An intraocular lens according to claim 1, wherein said coating layer is formed of an ultraviolet absorber mixed with a material which includes at least one material selected from the group consisting of hydrocarbons, nitro-compounds, amino-compounds, cyano compounds, silicone compounds, fluorine compounds and heterocyclic compounds.

4. An intraocular lens according to claim 1, wherein said ultraviolet absorber is an aromatic compound.

5. An intraocular lens according to claim 1 wherein said coating layer is directly on said at least said first surface of said lens base.

6. An intraocular lens according to claim 1 further comprising an intermediate layer directly on said at least said first surface of said lens base, and wherein said coating layer is on said intermediate layer such that said intermediate layer is between said coating layer and lens base.

* * * * *

UNITED STATES PATENT AND TRADEMARK OFFICE
CERTIFICATE OF CORRECTION

PATENT NO. : 5,026,395

DATED : June 25, 1991

INVENTOR(S) : Ikuo Nakajima, et al.

It is certified that error appears in the above-identified patent and that said Letters Patent is hereby corrected as shown below:

ON THE TITLE PAGE:

[56] References Cited

"Penman et al." should read --Peyman et al.--.
"Tiffony" should --Tiffany--.

COLUMN 4:

Line 4, "100 SCMM" should read --100 SCCM--.
Line 15, "minutes." should read --seconds.--.
Line 58, "long" should read --along--.

COLUMN 7:

Table 4

"boling" should read --boiling--.

Signed and Sealed this

Tenth Day of November, 1992

Attest:

DOUGLAS B. COMER

*Attesting Officer*     *Acting Commissioner of Patents and Trademarks*